United States Patent [19]
Harris

[11] 3,978,915
[45] Sept. 7, 1976

[54] CONDENSER WITH LEAK DETECTING APPARATUS

[75] Inventor: George A. Harris, Hialeah, Fla.

[73] Assignee: E. F. I. Inc., Miami, Fla.

[22] Filed: Dec. 28, 1973

[21] Appl. No.: 429,347

Related U.S. Application Data

[60] Division of Ser. No. 176,479, Aug. 31, 1971, Pat. No. 3,782,180, which is a continuation-in-part of Ser. No. 161,515, July 12, 1971, abandoned, which is a division of Ser. No. 736,917, May 20, 1968, Pat. No. 3,592,967.

[52] U.S. Cl.............................. 165/11; 73/69; 165/84
[51] Int. Cl.² ........................................ G01N 29/00
[58] Field of Search ................. 165/84, 11; 73/69

[56] References Cited
UNITED STATES PATENTS

| | | | |
|---|---|---|---|
| 2,514,797 | 7/1950 | Robinson | 165/84 X |
| 2,664,274 | 12/1953 | Worn et al. | 165/84 X |
| 3,042,481 | 7/1962 | Coggeshall | 165/84 X |
| 3,183,967 | 5/1965 | Mettenleiter et al. | 165/84 X |
| 3,312,274 | 4/1967 | Sebald | 165/11 X |
| 3,368,610 | 2/1968 | Kartlube et al. | 165/84 X |

FOREIGN PATENTS OR APPLICATIONS

| | | | |
|---|---|---|---|
| 532,144 | 1/1941 | United Kingdom | 165/84 |

*Primary Examiner*—Albert W. Davis, Jr.
*Attorney, Agent, or Firm*—Burmeister, York, Palmatier, Hamby & Jones

[57] ABSTRACT

This application discloses an apparatus for detecting leaks or thin spots in condenser tubes by means of ultra-sonic radiations. A number of ultrasonic generators is placed within the chamber or enclosure of the tubes of a condenser, and the generators transmit ultrasonic waves to flood the chamber with energy. A detector sensitive to the frequency of the ultrasonic waves is scanned over the open ends of the condenser tubes. When the detector is at the end of a tube having a hole or thin spot, the intensity of vibrations picked up by the detector will be relatively high, and thus the defective tube is located. A condenser particularly adapted to testing of the tubes thereof by this method is also disclosed.

4 Claims, 6 Drawing Figures

CONDENSER WITH LEAK DETECTING APPARATUS

This application is a division of application Ser. No. 176,479, filed Aug. 31, 1971, now U.S. Pat. No. 3,782,180 which is a continuation-in-part of application Ser. No. 161,515, filed July 12, 1971, now abandoned which is a division of application Ser. No. 736,917, filed on May 20, 1968, now U.S. Pat. No. 3,592,967, granted July 13, 1971.

The present invention relates to a method for detecting leaks in tubes, more particularly, condenser tubes, and to a steam condenser particularly useful in carry-out out the leak detecting method. More particularly, the invention relates to the use of ultrasonic vibrations for the detection of leaks.

In closed cycle steam plants, such as turbine steam plants for driving a ship, leakage must be very carefully watched. Steam is produced from distilled water for driving the turbine, and the spent steam is condensed and recycled in order to limit corrosion or buildup of deposits in the boiler or on the turbine. On a ship, sea water, or salt water is used for condensing spent steam and any leakage of salt water into the distilled water system must be avoided, and hence salinization probes at the condenser are provided to check the salt water content of the spent steam. These probes are sensitive, and on an indication of a low level of salt water in the spent steam, it becomes necessary to check the condenser for leaks in the walls between the spent steam and the sea water.

Prior to the present invention, a chemical compound that fluoresces green under an ultraviolet lamp has been used to check for leakage of condenser tubes. When the leaking tube or tubes are to be found, the condenser steam chamber is flooded with fresh water to which aforesaid aforersaid chemical compound has been added. The condenser tubes and the end chambers or manifolds at opposite ends of the tubes are drained of sea water, and compressed air is blown through the tubes to clear them of sea matter. An operator enters one of the end chambers with an ultraviolet lamp and checks each tube in sequence for liquid glowing green under the ultraviolet radiation from the lamp, thus indicating a leak. Tubes which are found to leak are then plugged, and noted for later repair. The steam plant may then be restored to operation.

There are a number of difficulties with this method of testing. One difficulty is that it may be cumbersome to flood the steam chamber of the condenser with water for the test, particularly if the turbine is at the same level as the steam chamber of the condenser, for in this event the turbine will have to be isolated from the condenser. Moreover, this method of testing places the fluorescing liquid under pressure whereas the tubes of the condenser are under vacuum in normal operation. Hence, it may require considerable time for the fluorescing liquid to appear through a small leak, or the leak may close entirely under pressure. Further, large leaks tend to result in the entire end of a bank of tubes fluorescing, thus making it difficult to isolate the leaky tube. Also, the fluorescing liquid will put in an appearance on the sea water side of the condenser only in the event that an actual leak is present. The fluorescent-liquid method does not work to indicate the presence of unsatisfactory thin spots in the condenser tubes.

The present invention further provides a distinct improvement over the detection method just described, in that it is unnecessary to spend the time and effort in flooding and subsequently draining the spent steam chamber of the condenser for testing. With permanently installed ultrasonic generators, the spent steam condenser chamber may retain its vacuum, and for installation of portable generators the spent steam chamber must merely be opened to atmospheric pressure in the present method.

Ultrasonic sound is radiated by the generators into the spent steam chamber of the condenser to flood the chamber. Since ultlrasonic energy is reflected by the walls of the chamber, standing waves will be established within the chamber, thus limiting the amount of energy which must be supplied to the chamber. Ultrasonic energy will pass through any aperture and hence can be picked up by a detector confronting the opposite side of the aperture. Further, a thin spot in a tube wall can be made to vibrate by ultrasonic energy, hence transmitting such energy through the wall where it can be detected by an ultrasonic detector.

These and further objects and advantages of the present invention will be more fully understood from the accompanying drawings, in which.

Figure 1:
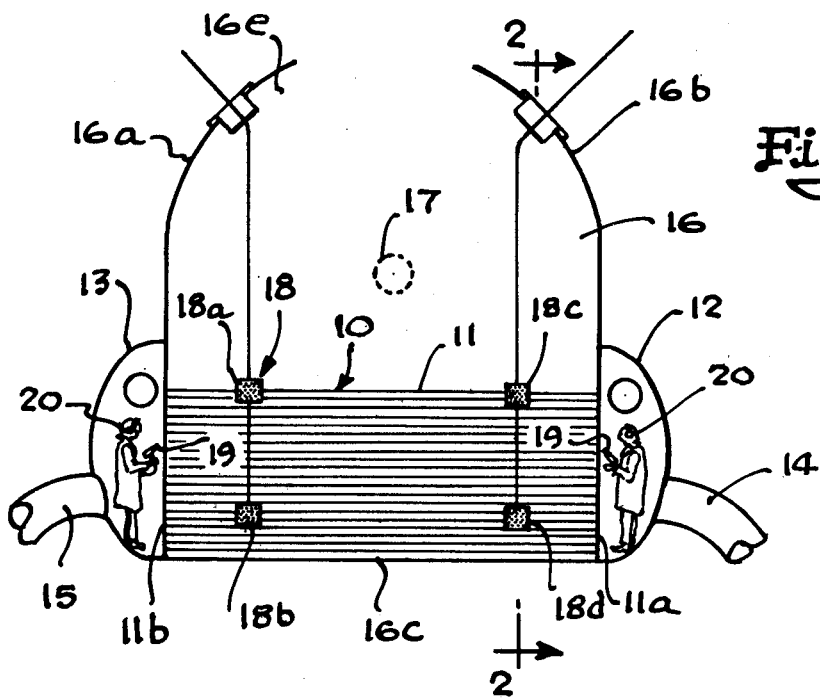
FIG. 1 is a longitudinal sectional view of a steam turbine ship condensing unit showing the manner in which the detecting method of the present invention is applied to the condenser thereof, the view being somewhat diagrammatic.
Figure 2:
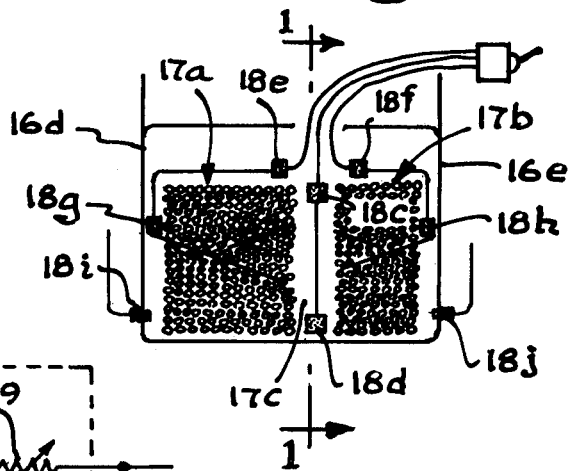
FIG. 2 is a fragmentary sectional view taken along the line 2—2 of FIG. 1.

As shown in FIG. 1, a condenser 10 has a plurality of spaced parallel hollow tubes 11 extending between walls 11a and 11b. Each tube 11 is sealed at its ends in openings in the walls 11a and 11b. The walls 11a and 11b also form one wall of headers 12 and 13 respectively. A sea water inlet 14 and an outlet 15 are connected to the headers 12 and 13 respectively. Above the condenser 10 is a chamber 16 disposed within an air tight enclosure 16a which is formed by the wall 11a and 11b, a rounded upper wall 16b, a bottom 16c and end walls 16d and 16e. The enclosure 16a contains a turbine (not shown) having a driving shaft 17, the chamber 16 also enclosing the exhaust steam from the turbine in operation. The condenser tubes 11 are disposed within the enclosure 16a and are divided into two banks 17a and 17b spaced one from another by a gap 17c. In the space 17c between the banks, a number of ultrasonic generators 18 are located, four such generators designated 18a, 18b, 18c and 18d being shown in FIGS. 1 and 2. FIG. 2 also illustrates one ultrasonic generator 18 disposed above each bank of tubes 17a and 17b, the generators 18e and 18f being disposed in the same plane as the generators 18c and 18d, although it is to be understood that one ultrasonic generator is also disposed above each bank of tubes 17a and 17b in the plane of generators 18a and 18b.

In addition, two ultrasonic generators 18 are disposed between the wall 16d and bank 17a, and two ultrasonic generators are disposed between the wall 16e and the bank 17b. Two of these ultrasonic generators are located in the plane of ultrasonic generators 18a and 18d (FIG. 2) and have been designated 18g and 18h, and it is to be understood that the other two ultrasonic generators are in the plane of ultrasonic generators 18a and 18b.

FIG. 2 also illustrates two ultrasonic generators 18i and 18j which are mounted in openings in the walls 16d and 16e, respectively, in the plane of generators 18c and 18d. Similar generators extend through the walls 16d and 16e in the plane of generators 18a and 18b.

The ultrasonic generators 18 must establish a level of ultrasonic energy within the enclosure 16a which is sufficient to penetrate any leak in a tube 11 or the seal between a tube and the wall 11a or 11b. This is possible because of the sound reflecting properties of the enclosure 16a and the tubes 11. As a result of reflections, any one ultrasonic generator 18 will establish a pattern of standing waves throughout the entire enclosure 16a, the regions of compression and rarification being spaced by distances of one wavelength from adjacent regions of compression or rarification, except for the effects of multiple reflections. The enclosure 16a, however, is not in practice constructed of perfect sound reflecting materials nor is it infinitely rigid, and as a result absorption of ultrasonic energy will result in degradation of the ultrasonic standing wave pattern, usually in regions remote from the generator. As a result, a plurality of ultrasonic generators 18 are employed to establish an ultrasonic wave pattern of adequate amplitude. The outputs of all generators, and the reflections thereof, add vectorially to produce a flooding of the interior of the enclosure 16a with ultrasonic energy.

Ultrasonic flooding of the enclosure 16a can be achieved in the presence of spent steam and also while the enclosure 16a is maintained under vacuum. It is necessary to shut down the steam plant, however, in order to permit draining of the tubes 11 and headers 12 and 13, but the conventional vacuum, or reduced pressure medium, in the turbine chamber may be maintained to permit the plant to be rapidly returned to operation and residual steam will not interfere with flooding the enclosure 16a with ultrasonic radiation. The ultrasonic standing wave pattern will not be stable, however, due to temperature and other instabilities, and it is preferable for testing purposes that the standing wave pattern be unstable.

The standing wave pattern will not be of uniform amplitude throughout a large enclosure 16a due to attenuation, and it is therefore desirable to place the ultrasonic generators 18 near areas expected to produce leaks. Most leaks occur in the regions of the tubes 11 in the first few inches of the inlet wall 11a, and hence the ultrasonic generators disposed in the plane of FIG. 2 are disposed closer to the wall 11a than to the center of the tubes 11. Likewise, there is an increased probability of leaks in the seals of the tubes 11 to the walls 11a and 11b. Location of the generators in the plane of generators 18a and 18b closer to the wall 11b assures adequate sound pressure at this wall also.

While it is preferable to permanently mount ultrasonic generators 18 within the enclosure 16a of the condenser, the tubes 11 and walls 11a and 11b may be tested for leaks and thin spots by positioning portable ultrasonic generators generally in the positions illustrated in FIGS. 1 and 2. It will of course be necessary to release the vacuum in the enclosure 16a in order to position the generators 18 for the tests, thus increasing the down time of the plane. Further, it is not necessary that 16 generators 18 be used, as illustrated in FIGS. 1 and 2, or that the ultrasonic generators be positioned as illustrated as long as the enclosure 16a is adequately flooded with ultrasonic energy.

The condenser of a steam plant is generally constructed of iron, usually in the form of cast iron or steel, with walls at least 1/8 inch thick. Iron is a good sound reflector since it is not absorbent to sound and is rigid. Greater thicknesses of walls increase rigidity and hence reduce loss of sound energy as a result of movement induced in the walls.

In each of the condenser headers 12 and 13, an operator is shown, holding an ultrasonic detector 19 having a headset 20 worn by the operator. The two operators are illustrated in the process of testing for leaks, as will be described hereinafter.

Figure 3:
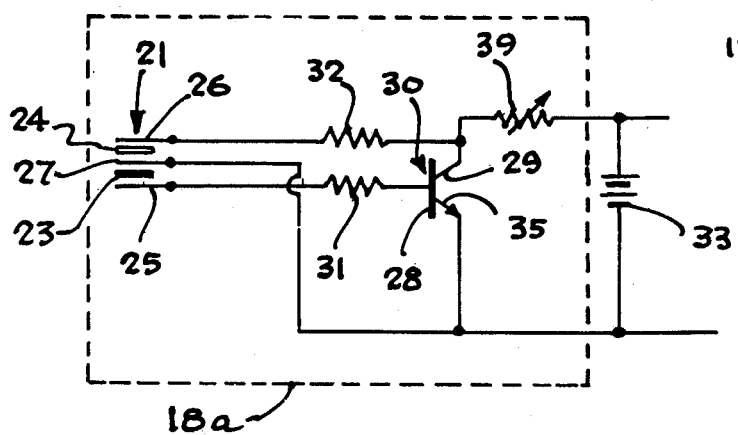
FIG. 3 is an electrical circuit of a unit of an ultrasonic generator used in the method of the present invention.

FIG. 3 illustrates schematically one unit 20a used in the generators 18 to generate the ultrasonic energy. Sonic waves are produced by an ultrasonic transducer 21 having a pair of members 23 and 24 of piezoelectric material disposed between two electrodes 25 and 26. A third electrode 27 of the ultrasonic transducer 21 is disposed between the members 23 and 24. The electrodes 25 and 26 are connected, respectively, to a base 28 and a collector 29 of a transistor 30 through resistors 31 and 32, respectively. The collector 30 is connected to the positive terminal of a power source, illustrated as a battery 33, through a variable resistor 34. Transistor 30 has an emitter 35 which is connected to the negative terminal of the battery 33. Electrode 27 of the ultrasonic transducer 21 is also connected to the negative terminal of the battery.

Figure 4:
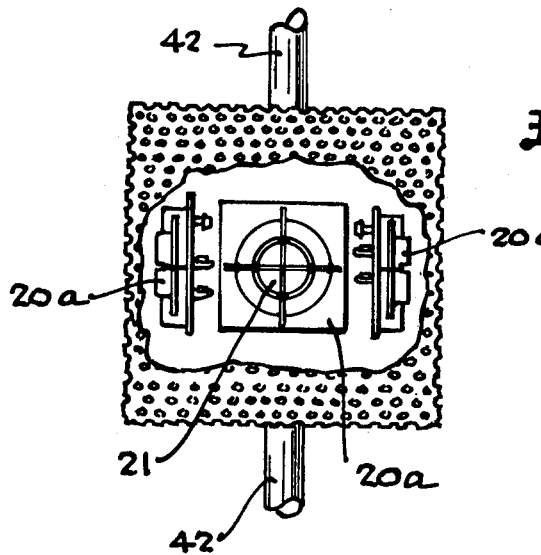
FIGS. 4 and 5 are elevational views of the ultrasonic generator partly broken away.
Figure 5:
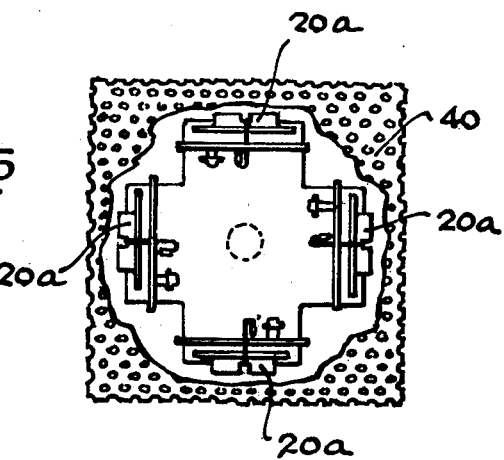

FIGS. 4 and 5 illustrate the mechanical construction of each sound source 18, except the sound sources 18i and 18j, and show four units 20a mounted within a hollow cube 40 of perforated solid material, i.e. expanded armor mesh. The four transducers 21 are directed outwardly from a common axis perpendicularly to four of the walls of the cube 40. A power cable 42 passes centrally through the other two walls of the cube 40 and conducts power from a remote source to the units, the source constituting the battery 33 and variable resistor 34 illustrated in FIG. 3. Sound sources 18i and 18j contain a single unit 20a and are designed to be screwed into the hole for a plug in the enclosure 16a.

Figure 6:
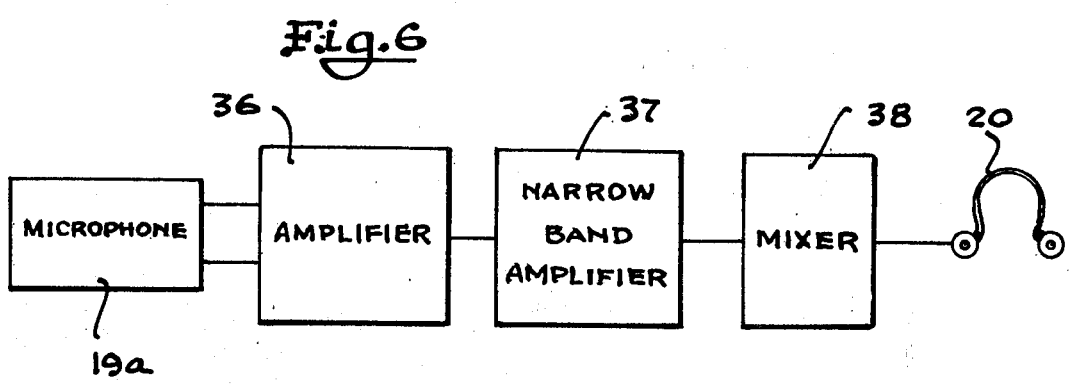
FIG. 6 is a schematic block diagram showing an ultrasonic detector for use in the present invention.

FIG. 6 diagrammatically illustrates an ultrasonic detector 19 suitable for use in testing for leaks according to the present invention. The detector 19 has a microphone 19a and it is connected in cascade with an amplifier 36, a narrow-band amplifier 37, a mixer 38 and an oscillator 44. The headset 20 is connected to the output of the mixer 38. The microphone 19a is responsive to ultrasonic energy which is amplified by the amplifier 36, isolated from other energy by the narrow-band amplifier 37, and converted to an audio frequency by the mixer 38 and oscillator 44. Hence, the presence of ultrasonic energy results in an audible tone in the headset 20 which is heard by the operator. Reference is made to Harris U.S. Pat. No. 3,592,967, dated July 13, 1971, column 3, lines 16 to 75, column 4, lines 1 to 57, for a more complete disclosure of how the amplifiers 36 and 37, mixer 38, and oscillator 44 operate between the microphone 19 and the headset 20.

The pass-band of the narrow-band amplifier 37 must include the frequency of the radiation from the ultrasonic sources 18. In addition, the pass-band is selected to isolate the headsets 20 from radiation from sources other than the sources 18. Energy in the ultrasonic range is generally suitable for the testing procedure here set forth, but the applicant has found that radiation with a frequency of about 40,000 cycles is particularly desirable. Radiation at this frequency has a relatively short wavelength resulting in standing waves with closely spaced regions of rarification or compression, which is desirable in locating leaks, and is unlikely to be at a frequency of some ambient noise.

When the condenser tubes 11 are to be tested for leaks, the tubes 11 and headers 12 and 13 are drained to the maximum possible extent, and the tubes 11 are blown out from the intake end with air under pressure. If ultrasonic sources 18 are permanently mounted within the enclosure 16a, these sources are energized to flood the enclosure 16a with ultrasonic energy. If the sound sources 18 must be placed in the enclosure 16a, the vacuum of the enclosure 16a is released and the inspection hatches on the steam side of the condenser are opened, and the ultrasonic generators 18 are inserted therethrough to the positions shown in FIGS. 1 and 2. Two operators with ultrasonic detectors 19 and a supply of corks enter the headers 12 and 13 and assume the positions shown in FIG. 1.

The ultrasonic generators 18 are maintained operative to maintain the level of ultrasonic energy within the enclosure 16a. The operators in the headers 12 and 13 position the detector 19 on the same tube at the same time, and move the detectors from tube to tube to scan all tubes. If there is a tube, or a plurality of tubes 11, with a hole or leak, ultrasonic waves will be picked up by the microphones 19a in the detectors 19 and transformed by the mixers 38 into audible sounds in the headsets 20 so that a tone will be heard by the operators, even though neither microphone 19a is right at the end of the leaking tube. When one microphone 19a finally reaches the end of a tube 11 having a hole or leak in it, the level of ultrasonic vibrations picked up in the microphone will be appreciably increased, as will the audible sound in the associated headset 20. The operator finding the leaking condenser tube 11 communicates this fact to the other operator by shouting to him down the tube, and the latter corroborates this by his own microphone 19a and headset 20. The operators temporarily plug the leaking tubes 11 with corks which absorb sound and isolate the headers 12 and 13 from the sound sources 18, thus permitting the operators to continue scanning the ends of the tubes without a background of radiation. The corks also act as markers for the men who come next to plug the leaking tubes permanently. A steam plant, as used in ocean going vessels has between 6,000 and 12,000 tubes, thus permitting plugging of many tubes before repairs become necessary.

In the same way, the condenser tubes 11 can be checked for thin spots. The power of the ultrasonic generators 18 is increased by lowering the resistance of the resistance 34 until the ultrasound is of sufficient intensity to vibrate thin spots in the metal of the tubes, but not areas of standard thickness.

The ultrasonic waves produced by the generators 18 are far above the range of human hearing and may be at the level of 40 kilocycles. These ultrasonic vibrations are transmitted in air or other gas, but not through solid material of appreciable thickness. Thus the ultrasonic vibrations cannot be detected or "heard" in the headers 12 and 13 of the condenser 10, in the absence of tube leaks or thin spots. The ultrasonic vibrations have the property that they can go around, over, or under any obstacle, and through any aperture, no matter how small or devious, but cannot pass through solids of appreciable thickness. The detectors 19 will pick up ultrasonic vibrations coming through thin spots or openings in the condenser tubes 11, but are not responsive to ordinary background noise.

The invention claimed is:

1. In a steam generating plant having a closed steam system with a steam condenser for spent steam, the improvement wherein the condenser comprises means constructed of ultrasonic radiation reflecting material defining a closed chamber connected in the steam system to receive spent steam and containing a gaseous medium including a first wall having a plurality of apertures therein, a second wall having a plurality of apertures therein equal in number to the apertures in the first wall, a first header sealed to the first wall spaced from and confronting the apertures in the first wall, a second header sealed to the second wall spaced from and confronting the apertures in the second wall, a plurality of hollow tubes equal in number to the number of apertures in the first and second walls, each tube having one end sealed in one of the apertures of the first wall and the other end sealed in one of the apertures of the second wall, and means mounted within the chamber having a radiator coupled to the gaseous medium in the chamber for generating standing waves of ultrasonic energy within the gaseous medium of the chamber, whereby the apertures in the first wall may be scanned with an ultrasonic detector disposed in the first header and the apertures in the second wall may be scanned with an ultrasonic detector disposed in the second header to determine the magnitude of ultrasonic leakage from the chamber through each of the tubes as an indication of fluid leaks from the chamber or thin spots in the hollow tubes.

2. The combination comprising claim 1 wherein a plurality of ultrasonic sound radiators are mounted within the chamber, one sound radiator being disposed closer to the first wall than the second wall and another sound radiator being disposed closer to the second wall than the first wall.

3. The combination of claim 2 wherein the tubes are disposed parallel to each other and grouped in a plurality of adjacent banks of tubes, and wherein a sound radiator is disposed between adjacent banks of tubes.

4. The combination of claim 2 wherein a sound radiator is sealed within an opening in the means defining a closed chamber.

* * * * *

UNITED STATES PATENT OFFICE
CERTIFICATE OF CORRECTION

Patent No. 3,978,915　　　　　Dated September 7, 1976

Inventor(s) George A. Harris

It is certified that error appears in the above-identified patent and that said Letters Patent are hereby corrected as shown below:

Column 1, line 39, after "which" delete "aforesaid" and insert -- the --; same line 39, "aforersaid" should read -- aforesaid --. Column 4, line 1, "plane" should read -- plant --.

Signed and Sealed this

Sixteenth Day of November 1976

[SEAL]

Attest:

RUTH C. MASON
Attesting Officer

C. MARSHALL DANN
Commissioner of Patents and Trademarks